United States Patent
Lubart

(12) 
(10) Patent No.: US 6,379,376 B1
(45) Date of Patent: Apr. 30, 2002

(54) DEVICE FOR LIGHT IRRADIATION ONTO TISSUE

(76) Inventor: Rachel Lubart, Hankin Street 10, Tel Aviv 62506 (IL)

(*) Notice: Subject to any disclaimer, the term of this patent is extended or adjusted under 35 U.S.C. 154(b) by 0 days.

(21) Appl. No.: 09/308,773

(22) PCT Filed: Nov. 18, 1997

(86) PCT No.: PCT/IL97/00375

§ 371 Date: May 25, 1999

§ 102(e) Date: May 25, 1999

(87) PCT Pub. No.: WO98/23329

PCT Pub. Date: Jun. 4, 1998

(30) Foreign Application Priority Data

Nov. 25, 1996 (IL) .................................................. 119683

(51) Int. Cl.[7] .............................. A61N 5/06; A61B 18/18
(52) U.S. Cl. .................................. 607/88; 606/2; 606/9
(58) Field of Search .............................. 606/2, 3, 9, 10, 606/13–17; 607/88, 89, 92, 93

(56) References Cited

U.S. PATENT DOCUMENTS

| | | | |
|---|---|---|---|
| 1,856,969 A | * 5/1932 | Reiter et al. | |
| 3,818,914 A | * 6/1974 | Bender | |
| 4,401,651 A | * 8/1983 | Knutson | |
| 4,874,361 A | * 10/1989 | Obagi | 604/20 |
| 4,909,254 A | 3/1990 | Wilkinson | |
| 4,930,504 A | * 6/1990 | Diamantopoulos et al. | |
| 4,951,663 A | * 8/1990 | L'Esperance, Jr. | |
| 5,030,200 A | 7/1991 | Judy et al. | |
| 5,464,436 A | * 11/1995 | Smith | 607/89 |
| 5,824,023 A | * 10/1998 | Anderson | 607/88 |
| 5,849,027 A | * 12/1998 | Gart et al. | 607/93 |
| 5,913,884 A | * 6/1999 | Trauner et al. | 607/88 |
| 5,964,749 A | * 10/1999 | Eckhouse et al. | 606/9 |

FOREIGN PATENT DOCUMENTS

| | | |
|---|---|---|
| IL | 087915 | 3/1992 |
| IL | 100545 | 3/1995 |
| IL | 102125 | 4/1997 |
| WO | 8908474 | 9/1989 |
| WO | 9113652 | 9/1991 |
| WO | 9519810 | 7/1995 |

OTHER PUBLICATIONS

Chavrier et al., "Laser a infra–rouge et cicatrisation conjonctive en chirurgie parodontale", *J. Parod.* vol. 5, pp. 209–212, (1986).

Mester et al., "Clinical results of laser stimulation and experimental studies on the mechanism of action" *Minerva Medica*, vol. 72, pp. 2195–2199, (1981).

Grossman et al., "Visible Light Promotes Proliferation of Normal Skin Cells", *J. Invest. Dermatol*, vol. 102 649A, (1994).

Kjeldstad, "Photoinactivation of Propionibacteriumm acnes by Near–Ultraviolet Light", vol. 39, vol. 300–302 (1984).

Melo et al., "Photodestruction of Propionibacterium acnes Porphyrins", *Z. Naturforsch*, vol. 40c, pp. 125–128 (1985).

(List continued on next page.)

*Primary Examiner*—Roy Gibson
(74) *Attorney, Agent, or Firm*—Browdy and Neimark, PLLC

(57) ABSTRACT

A method and device for inducing or promoting growth and proliferation of skin cells or tissue or for controlling bacterial skin infection is described. The skin cells are irradiated with a low-intensity broad spectrum light at a wavelength of between about 340 to 3,000 nm. The increase in rate of cultivated cells is useful for example to obtain skin-like tissue needed for skin grafts or for promoting healing of skin wounds or lesions. Light-induced skin bacteria control is useful for example in the treatment of bacterial infections of the skin.

24 Claims, 2 Drawing Sheets

OTHER PUBLICATIONS

Lyons et al., "Biostimulation of Wound Healing in Vivo by a Helium–Neon Laser", *Ann. Plast. Surg.*, vol. 18 pp. 47–50, (1987).

Surinchak et al., "Effect of Low–Level Energy Laser on the Healing of Full–Thickness Skin Defects", *Lasers in Surgery and Medicine*, vol. 2, pp. 267–274, (1983).

Lubart et al., "Effects of Visible snd near–infrared lasers on cell cultures", *J. Photochem. Photobiol. B. Biol.*, vol. 12, pp. 305–310, (1992).

Lubart et al., "Light Effect on Fibroblast Proliferation", *Laser Therapy*, vol. 5, 55–57, (1993).

* cited by examiner

DEVICE FOR LIGHT IRRADIATION ONTO TISSUE

CROSS REFERENCE TO RELATED APPLICATION

The present application is the national stage under 35 U.S.C. 371 of PCT/IL97/00375, filed Nov. 18, 1997.

FIELD OF THE INVENTION

The present invention concerns a method and device for affecting growth and proliferation of cells or tissue by light irradiation. The device and method of the invention are useful in increasing the rate of growth and proliferation of skin epithelial cells. Another use of the inventive device and method is the controlling bacterial infections of the skin, e.g. in the case of acne vulganison. The device and method of the invention may thus be employed in the treatment of skin, oral or vaginas wounds or lesions, as well as irradiating keratinocytes in culture to increase the yield of the culture.

In the following, irradiation of light intended to increase rate of growth and proliferation of cells will be referred to herein at times as "light-induced growth acceleration"; treatment for the purpose of control of bacterial infections will be referred to herein at times as "light-induced bacteria control"; treatment of skin or oral wounds or lesions by light irradiation for the purpose of accelerating healing, will be referred to herein at times as "light therapy".

LIST OF PRIOR ART

The following is a list of prior art considered to be relevant as a background to the invention:
1. Mester, E.: Clinical results of laser stimulation and experimental studies on the mechanism of action *Minerva Med.*, 72:2195–2199 (1981).
2. Lyons R. F., Abergel, R. P., White, R. A., Dwyer R. M., Castel, J. C., Uitto, J.: Biostimulation of wound healing in vivo by Helium-neon laser, *Ann. Plast. Surg.*, 18:47–50 (1987).
3. Surinchak, J. S., Alago, M. L., Bellamy R. F., Stuck, B. E., Belkin, M.: Effects of low-level energy lasers on the healing of full-thickness skin defects, *Lasers Surg. Med.*, 2:267–274 (1983).
4. Chavrier, C., Hartmann, S., Couble M. L., Msloire H.: Laser a infra-rouge et cicatrisation conjunoctive en chirurgie parodontale, *J. Parod.*, 5:209–212 (1986).
5. Lubart R., Wollman, Y, Friedman, H: Effects of visible and near IR lasers on cell cultures, *J. Photochem. Photobiol. B. Biol.*, 12:305–311 (1992).
6. Lubart, R., Friedman, H., Peled, I, Grossman, N: Light effect on fibroblast proliferation, *Laser Therapy*, 5:55–57 (1993).
7. Grossman, N., Reuveni, H., Halevy, S., Lubart, R: Visible light promotes proliferation of normal skin cells, *J. Invest. Dermatol.*, 102:649A (1994).
8. Kjeldstad B., Photoinactivation of propionibacterium acnes by near UV light, Z. Naturfersch 39(C):300–302 (1984).
9. Relø, T. B., Reisaeter G., and Johnson, A., Photodestruction of propionibacterium acnes porphysins, Z. Naturfersch, No. C 125–128 (1985).

The above prior art documents will be referred to in the text by indicating their numbers from the above list within brackets. It should be noted that the acknowledgement of these references herein does not amount to an indication that these are by any way relevant to the issue of patent-ability of the appended claims.

BACKGROUND OF THE INVENTION

Light therapy using low energy visible or near infrared light sources has been known to have a beneficial biological effect on a variety of tissues. Thus, during the last decade, low energy lasers (LEL) were introduced in treatment of wounds or lesions in a variety of tissue. LEL (mainly He—Ne lasers) has been proven effective in patients in promoting epithelization in full thickness skin defects, as well as for gynecological problems and lesions in oral epithelia[1,2,3,4].

In treatment of acute massive burn wounds, particularly such that cover large portions of the body area, it is necessary to bring to regrowth of skin over the burnt area, the standard medical practice of grafting of autologous tissue is very often complicated by the relative shortage of autologous donor sites. A primary advance towards this problem has been the development of an in vitro cultivation technique for human epidermal keratinocytes. The main disadvantage of such cultivation methods is that it requires a period of three to six weeks to obtain sufficiently large quantities of cultured tissue ready for grafting.

Studies with skin derived cultured cells (normal human fibroblasts and keratinocytes) showed that irradiation of visible, near infrared or near ultraviolet (UVA) light at low energy densities, was effective in promoting proliferation of the cells; against this, irradiation at higher energy densities inhibited cell growth[5,6,7]. Light in the UVA and in the visible light range was found to destroy bacteria such as Propionibacterium acnes[8,9]. Radiation sources used hitherto included a variety of monochromatic and non-monochromatic light sources, irradiated at a wavelength of 360 nm (UVA), 540 nm and 600–900 nm, as well as HeNe 632 nm lasers and 780 nm diode lasers. It should be noted that similar light sources are used for selective destruction of tumors by photoactivation of sensitizing drugs, in a technique known as photodynamic therapy (PDT).

A common problem associated with all prior art used light sources is that they are relatively complicated and expensive, and not readily available to physicians.

SUMMARY OF THE INVENTION

It is the object of the invention to provide a method and device for light induced growth modulation of skin or epithelial cells.

It is an object in accordance—with one embodiment of the invention to provide such a method and device for light-induced growth acceleration of skin or epithelial cells, such as fibroblasts and keratinocytes, in culture.

It is an object in accordance with another embodiment of the invention to provide a method and device for light-induced bacteria control on the skin as an epithelium, e.g. and or vaginal epithelium.

It is an object in accordance with a further embodiment of the invention to provide a method and device useful in light therapy of wounds or lesions.

The present invention provides, by a first of its aspects, a method of inducing or promoting growth and proliferation of skin cells or tissue or for controlling bacterial skin infection, comprising irradiating the skin cells with a low-intensity broad spectrum light at a wavelength between about 340 to 3,000 nm.

The present invention provides, by another of its aspects, a device for use in promoting or inducing growth and proliferation of skin cells or for controlling bacterial skin infection, the device comprising a light source which comprises a lamp emitting a broad spectrum light at a wavelength between about 360 to 3,000 nm. The device may further comprise a focusing assembly as well as a light filtration assembly.

For some uses, e.g. irradiation onto wounds or lesions within the mouth or vaginas, the device may be equipped with a fiber optic so as to deliver the light to the desired site.

In accordance with one embodiment, the method and device are used for light-induced growth acceleration cells, e.g. skin cells, in culture, i.e., to induce or promote growth and proliferation of these cells. The device and method in accordance with this embodiment are particularly useful in increasing the rate of cultivation of such cells in order to rapidly obtain skin-like tissue for grafting onto burn wounds. The device in accordance with this embodiment may comprise a lens adapted to diffuse the light onto the entire surface of the culture, or means to move the light skin, periodically across the culture.

In accordance with another embodiment, the method and device are used for light-induced skin bacteria control. Skin bacteria control includes destruction of bacterial cells, as well as arresting growth and proliferation of the bacteria. It was found in accordance with the invention that the destruction of bacteria by light irradiation is improved in an oxygen rich environment; accordingly by a preferred embodiment of the invention the bacteria skin control is a combined irradiation and oxygen flows into the skin. By another preferred embodiment the oxygen is supplied as a peroxide, e.g. $H_2O_2$.

In accordance with another embodiment of the invention, the method and device are utilized for light therapy of skin as epithelium for inducing or promoting healing of skin wounds or lesions.

DETAILED DESCRIPTION OF THE INVENTION

Unlike the prior art, the present invention utilizes a light source, which is not coherent and not polarized and is capable of irradiating relatively large tissue areas. In order to induce a positive, i.e. a regeneration stimulating effect on the skin or epithelium, the light intensity should preferably be below about 800 mW/cm². It is clear however that for effective light therapy, the light intensity cannot be too low since otherwise there will likely be no effect. Typically, a lower limit of light intensity would be about 1 mW/cm². A preferred range of light intensity is 10–200 mW/cm².

The light source used in accordance with this invention emits, a "white" light, i.e. a light source emitting light of a broad spectrum covering the entire visible and optionally also the near infrared spectrum. An example of such a light source is a halogen lamp which emits light at wavelengths within the range of 340 to 3,000 nm. In order to avoid heating of the target, the IR portions of the emitted light may typically be filtered out so as to obtain light irradiation on the target at a wavelength within the range of about 340 to 1,200 nm, preferably within the range of about 340 to 800 nm.

In addition, the light may also be filtered through a UV filter for filtering out this harmful portion of the spectrum, thereby increasing safety.

The device in accordance with the invention may typically also comprise a lens for focusing the light onto the target cells or tissue.

Light may be irradiated either continuously or in pulses. Continuous light irradiation will typically be preferred in lower light intensities while pulsed irradiation will be preferred in higher light intensities. The decision whether to use constant irradiation of pulsed light irradiation depends on the exact application and on the total desired irradiation.

It will no doubt be clear to the artisan that the effect of the light depends both on the light intensity as well as on the duration of irradiation. In other words, high intensity irradiation requires a lower duration than a low intensity irradiation. Clearly, when depending on the duration of a pulsed light the net light time should be factored.

The effect of irradiation may at times be enhanced by the addition of photosensitizer substances to the target cells or tissue. For example, a culture of fibroblasts or keratinocytes may be supplemented with small amounts of a photosensitizer substance, such as hematoporphyrin derivatives prior to light irradiation. Such substances may also be applied topically onto the skin prior to the light therapy. The concentration of such substance is typically substantially lower than concentrations used in photodynamic therapy.

The invention will be illustrated further by the following examples:

EXAMPLE 1

3T3 NIH fibroblast cells were seeded in 25 or 96 multi-well plates. The concentration of cells was about 2.5× $10^3$–$10^4$ cells/well, respectively. 48 hours later cells were washed and exposed to light from a light source consisting of a 40 mW/cm² halogen lamp for various periods of time (in triplicate) while in the phosphate buffered saline (PBS). Following irradiation, the cultures were replenished with fresh growth media and were further incubated for 24–72 hours. At the end of the incubation, the cultures were washed with PBS and trypsinized.

Figure 1:
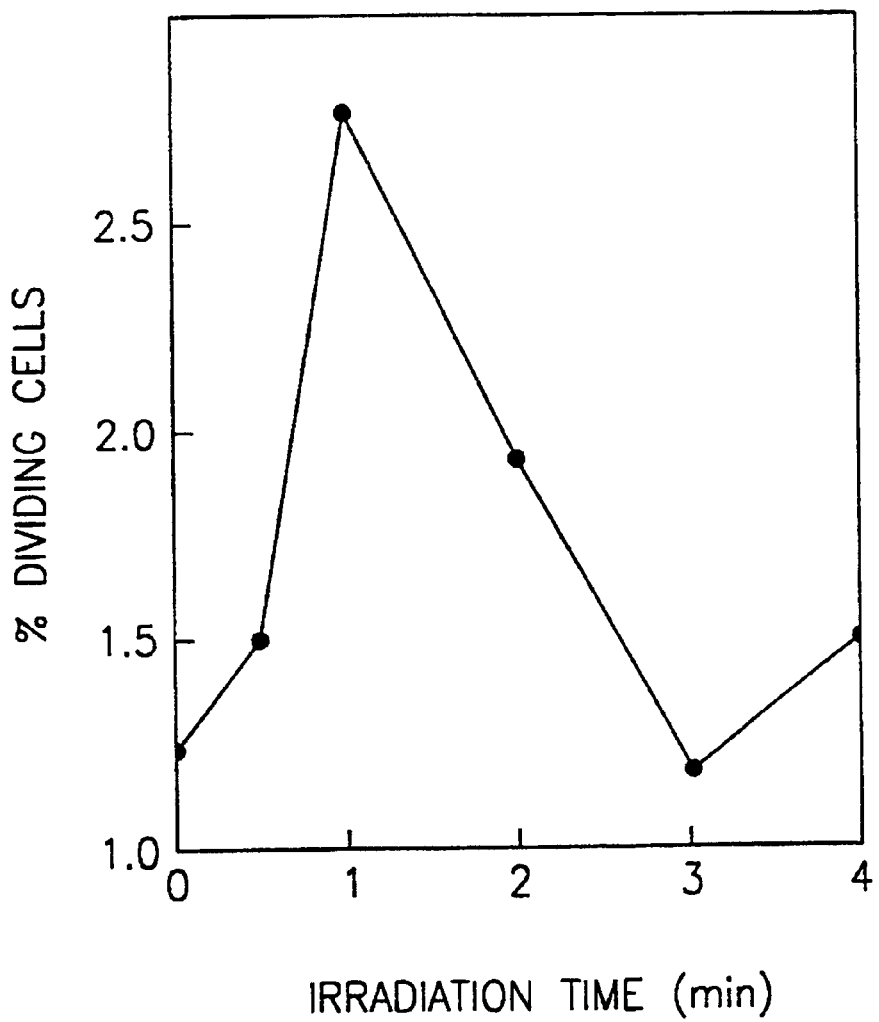
FIG. 1 is a schematic representation showing the percent of dividing fibroblast cells following their irradiation with a light source consisting of a 40 mW/cm² halogen lamp.

FIG. 1 shows the percent of proliferating cells that were divided 24 hours after irradiation. As can be seen, the number of dividing cells peaked in the culture which had been previously irradiated with the light source for 1 min.

This experiment demonstrates that irradiation of keratinocytes with light emitted from a halogen lamp accelerates growth and proliferation of these cells. This may be useful in growing tissue for skin grafts, wherein appropriate irradiation of the cells may result in a decrease in the time required to obtain a specific amount of such in vitro growth tissue.

EXAMPLE 2

17 young individuals who had adolescent wounds were treated by irradiation of their facial skin, using a device in accordance with the invention. The treatment of each individual consisted of three irradiations per week, each one with a light intensity of 40 mW/cm² for two minutes on the infected area.

The tested individuals reported dramatic improvement in their facial conditions and examination of the individuals showed that after this treatment, their faces had no wounds and no scars.

This clearly demonstrates the beneficial effect of irradiation with a halogen lamp on the treatment of skin wounds or lesions.

EXAMPLE 3

Individuals with adolescent wounds were treated by irradiating their facial skin similarly as in Example 2. A 2–3% $H_2O_2$ solution was applied onto the skin shortly before the irradiation.

A marked improvement in the individual's condition was observed.

EXAMPLE 4

50 individuals who had Herpes on their lip were treated twice or three times a day with the light source as described above. Each treatment was at 120 mW/cm$^2$ for 2 mins. Two to three days after beginning of the treatment, a significant improvement (decrease in severity of infection) was observed.

EXAMPLE 5

Figure 2:
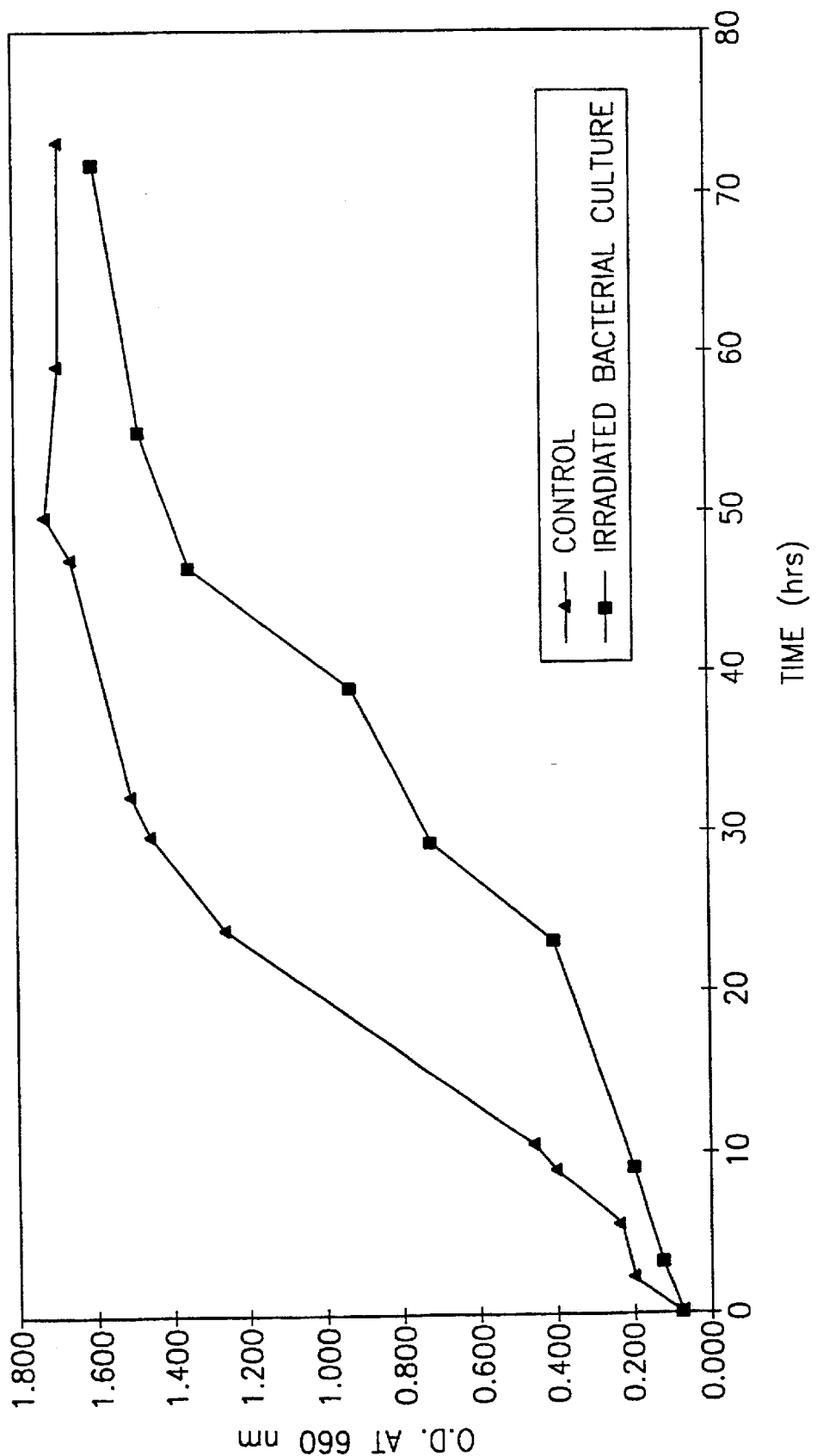
FIG. 2 is a schematic representation showing the optical density (OD) at 660 nm of propionibacterium acne cultures at various periods of time following their irradiation with a light source at 550 mW/cm² for 90 mins. The OD of the irradiated cultures was compared to a similar culture which was not subjected to irradiation.

Cultures of propionibacterium acnes were irradiated with the light source described above at 550 mW/cm$^2$ for 90 mins. As seen in FIG. 2, irradiation of the cells resulted in inhibition of their growth as compared to no-irradiated control cells.

What is claimed is:

1. A method of inducing or promoting growth and proliferation of cells or tissue, comprising irradiating the cells or tissue with a low-intensity broad spectrum light at wavelengths between about 340 to 3,000 nm with a light intensity and for a time selected to induce or promote proliferation of the cells or tissue, provided that if the lower limit of the wavelength spectrum is 600 nm, the upper limit is other than 900 nm.

2. A method according to claim 1, wherein the light irradiation is at a light intensity of below about 800 mW/cm$^2$.

3. A method according to claim 2, wherein the light intensity is at a range of about 10 to 200 mW/cm$^2$.

4. A method according to claim 1, wherein the cells are cultured skin cells.

5. A method according to claim 1, for treatment of skin in order to induce or promote healing of skin wounds and lesions wherein the skin is constituted by the cells or tissue.

6. A method according to claim 5, further comprising applying oxygen or a peroxide solution onto the skin.

7. The method of claim 1 wherein the broad spectrum light is white light.

8. The method of claim 1 further comprising applying to the cells or tissue a photosensitive substance selected to enhance the effect of the light.

9. A method for controlling bacterial infections of skin or epithelium comprising irradiating the skin or epithelium with a low-intensity broad spectrum light at wavelengths between about 340 to 3,000 nm with a light intensity and for a time selected to control bacterial infections of the skin or epithelium.

10. A method according to claim 2, wherein the wavelength of the light is between about 340 to 1,200 nm.

11. The method of claim 9 wherein the broad spectrum light is white light.

12. The method of claim 9 further comprising applying to the skin or epithelium a photosensitive substance selected to enhance the effect of the light.

13. A method of inducing or promoting growth and proliferation of cells or tissue comprising:
(a) selecting cells or tissue in which growth and proliferation are to be induced or promoted; and
(b) irradiating the selected cells or tissue with a low-intensity broad spectrum light at wavelengths between about 340 to 3,000 nm, provided that the irradiation is not with a broad spectrum light at 600–900 nm, thus inducing or promoting growth and proliferation of the selected cells or tissue.

14. The method of claim 13 wherein the broad spectrum light is white light.

15. A method of inducing or promoting growth and proliferation of cells or tissue, comprising irradiating the cells or tissue with at least one low-intensity broad spectrum light covering an entire spectrum between a lower wavelength of 340 nm or more and an upper wavelength of 3,000 nm or less with a light intensity and for a time selected to induce or promote proliferation of cells or tissue, provided that if the lower limit of the wavelength spectrum is 600 nm, the upper limit is other than 900 nm.

16. The method of claim 15 wherein the broad spectrum light is white light.

17. A method of inducing or promoting growth and proliferation of cells or tissue comprising:
(a) selecting cells or tissue in which growth and proliferation are to be induced or promoted; and
(b) irradiating the selected cells or tissue with at least one low-intensity broad spectrum light covering an entire spectrum between a lower wavelength of 340 nm or more and an upper wavelength of 3,000 nm or less, provided that the irradiation is not with a broad spectrum light at 600–900 nm,
thus inducing or promoting growth and proliferation of the selected cells or tissue.

18. The method of claim 17 wherein the broad spectrum light is white light.

19. A method of controlling bacterial infections of skin or epithelium comprising:
(a) selecting skin or epithelium in which bacterial infections are to be controlled; and
(b) irradiating the selected skin or epithelium with a low-intensity broad spectrum light at wavelengths between about 340 to 3,000 nm,
thus controlling bacterial infections of the selected skin or epithelium.

20. The method of claim 19 wherein the broad spectrum light is white light.

21. A method of controlling bacterial infections of skin or epithelium, comprising irradiating the skin or epithelium with at least one low-intensity broad spectrum light covering an entire spectrum between a lower wavelength of 340 nm or more and an upper wavelength of 3,000 nm or less with a light intensity and for a time selected to control bacterial infections of the skin or epithelium.

22. The method of claim 21 wherein the broad spectrum light is white light.

23. A method of controlling bacterial infections of skin or epithelium comprising:
(a) selecting skin or epithelium in which growth and proliferation are to be induced or promoted; and
(b) irradiating the selected skin or epithelium with at least one low-intensity broad spectrum light covering an entire spectrum between a lower wavelength of 340 nm or more and an upper wavelength of 3,000 nm or less,
thus inducing or promoting growth and proliferation of the selected skin or epithelium.

24. The method of claim 23 wherein the broad spectrum light is white light.

* * * * *